US008961433B2

(12) United States Patent
Patel et al.

(10) Patent No.: US 8,961,433 B2
(45) Date of Patent: Feb. 24, 2015

(54) CATHETER AND SYSTEM FOR CONTROLLING SAME

(75) Inventors: Rajnikant V. Patel, London (CA);
Jagadeesan Jayender, London (CA);
Suwas Nikumb, London (CA)

(73) Assignee: The University of Western Ontario, London, ON (CA)

(*) Notice: Subject to any disclaimer, the term of this patent is extended or adjusted under 35 U.S.C. 154(b) by 0 days.

(21) Appl. No.: 12/986,001

(22) Filed: Jan. 6, 2011

(65) Prior Publication Data

US 2011/0301615 A1 Dec. 8, 2011

Related U.S. Application Data

(63) Continuation of application No. 11/510,846, filed on Aug. 28, 2006, now abandoned.

(51) Int. Cl.
*A61B 5/00* (2006.01)
*A61M 25/01* (2006.01)
*A61L 29/04* (2006.01)
*A61L 29/14* (2006.01)

(52) U.S. Cl.
CPC ............ *A61M 25/0105* (2013.01); *A61L 29/04* (2013.01); *A61L 29/14* (2013.01); *A61L 2400/16* (2013.01)
USPC ...................................... 600/585; 604/95.05

(58) Field of Classification Search
USPC ........................................ 600/585; 604/95.05
See application file for complete search history.

(56) References Cited

U.S. PATENT DOCUMENTS

| 6,059,506 A * | 5/2000 | Kramer .............................. 414/5 |
| 6,547,757 B1 | 4/2003 | Kranz et al. |
| 6,702,809 B1 * | 3/2004 | Knopp et al. ................... 606/10 |
| 6,817,973 B2 | 11/2004 | Merril et al. |
| 6,875,170 B2 * | 4/2005 | Francois et al. ............. 600/141 |
| 2007/0239138 A1 * | 10/2007 | Lawrence et al. ............. 604/531 |

FOREIGN PATENT DOCUMENTS

| JP | 2001258827 | 5/1997 |
| JP | 09135907 | 9/2001 |

OTHER PUBLICATIONS

Jayender Modelling and Gain Scheduled Control.*
Peirs "Micro optical Force Sensor".*
Peirs et al. A Micro Optical Force Sensor for Force Feedback During Minimally Invasive Robotic Surgery. MME Nov. 2, 2003. pp. 211-214.
Jayender et al. Modelling and Gain Scheduled Control of Shape Memory Alloy Actuators. IEEE Conference on Control Applications. Aug. 28, 2005. pp. 767-772.

* cited by examiner

*Primary Examiner* — Max Hindenburg
*Assistant Examiner* — Renee Danega
(74) *Attorney, Agent, or Firm* — Hill & Schumacher

(57) ABSTRACT

The present invention describes a system for controlling a thin flexible thermoplastic catheter. The system includes a plurality of shape memory alloy filaments attached to the distal end of the catheter, each filament having a phase and a temperature; a means for receiving a strain value for at least one of the filaments; a means for determining the phase change that will results in the strain value, whereby the phase change is dependent on the temperature and the temperature is dependent on a voltage; and a means for setting the voltage in each filament thereby resulting in movement of the catheter. In addition, a three-degrees of freedom force sensor measures the magnitude and direction of the force exerted on the tip of the catheter. The catheter can be autonomously guided or it can be interfaced to a haptic device. The catheter can also be fitted with microtools.

33 Claims, 12 Drawing Sheets

CATHETER AND SYSTEM FOR CONTROLLING SAME

FIELD OF THE INVENTION

This invention relates to catheters and in particular a haptically controlled active catheter instrumented with shape memory alloy actuators and a three degrees of freedom force sensor.

BACKGROUND OF THE INVENTION

Angioplasty is a minimally invasive procedure that involves the insertion of a catheter into the blood vessel for removal of blockages in blood flow. In the conventional approach, the catheter is inserted into the body through the femoral artery and is guided through the lumen of the blood vessel till it reaches a blockage. A stent (superelastic Shape Memory Alloy) is then deployed to open the blood vessel at the blockage and let normal blood flow resume. The surgeon is provided with images that are obtained either by X-ray imaging or by Magnetic Resonance Imaging. These images enable the healthcare provider to track the end point of the catheter (position in absolute coordinates) in real time and determine the future course of insertion.

There are a number of problems associated with the conventional way of performing angioplasty. Specifically, the catheter insertion completely depends on the expertise and dexterity of the surgeon. In the case of intravascular neurosurgery, the catheter is pushed through extremely delicate and complex cranial blood vessels to treat aneurisms in the brain. The repeated insertion of the catheter through several trials could tear the blood vessel at the junction and cause heavy bleeding. This could also result in prolonged operating times and fatigue to clinicians and patients.

The surgeon has no method of estimating the amount of force that is being applied by the tip of the catheter on the walls of the blood vessel. Excessive pressure could rupture the blood vessel with dire consequences. Plaque could also be dislodged which may block blood vessels in the brain or heart and cause a stroke or a myocardial infarction.

The healthcare provider could have prolonged exposure to radiation or be subjected to a high-level of noise caused by the machinery generating magnetic fields for MRI. These pose danger or discomfort to the healthcare providers who perform the procedure over a prolonged period of time.

Another problem with the present procedure of Angioplasty is restenosis. The deployment of a stent at the site of a blockage only provides a temporary solution for resuming blood flow. In 40% of the procedures already done, the plaque begins to build up after a couple of years, a process called restenosis. In addition, the stent, made of superelastic Shape Memory Alloy, has a life of only 10 years. For these reasons, there may arise a need to perform repeated angioplasties for a single patient.

Accordingly it would be advantageous to provide a catheter wherein the movement of the tip can be controlled. Further it would be advantageous to provide a three degree of freedom force sensor that can be attached to a catheter.

SUMMARY OF THE INVENTION

The present invention describes a system for controlling a thin flexible thermoplastic catheter. The system includes a plurality of shape memory alloy filaments attached to the distal end of the catheter, each filament having a phase and a temperature; a means for receiving a strain value for at least one of the filaments; a means for determining the phase change that will result in the strain value, whereby the phase change is dependent on the temperature and the temperature is dependent on a voltage; and a means for setting the voltage in each filament thereby resulting in the bending of the catheter.

In another aspect of the invention there is provided a three dimensional force sensor adapted to be attached to the distal end of a catheter. The sensor includes a two-dimensional optical position sensing detector, a spring, an optical fibre embedded within the catheter and a means for determining the position of the beam spot on the detector. The two-dimensional optical position sensing detector is spaced from the distal end of the catheter. The spring attaches the detector to the catheter whereby a force acting on the detector moves the detector relative to the distal end of the catheter. A light beam is emitted from the end of an optical fibre that is embedded within the lumen of the catheter.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Researchers in the past have tried to instrument the catheter with Shape Memory Alloy actuators to actively control the tip of the catheter. This way the catheter can be smoothly guided into a branch in the blood vessel. The problem, however, is that the active catheters developed so far consist of actuators without any position feedback. Since most actuators used for the active catheter have a non-linear behavior, the control of the catheter by means of a joy-stick is extremely difficult and inaccurate and could cause damage to the blood vessels.

Figure 1:
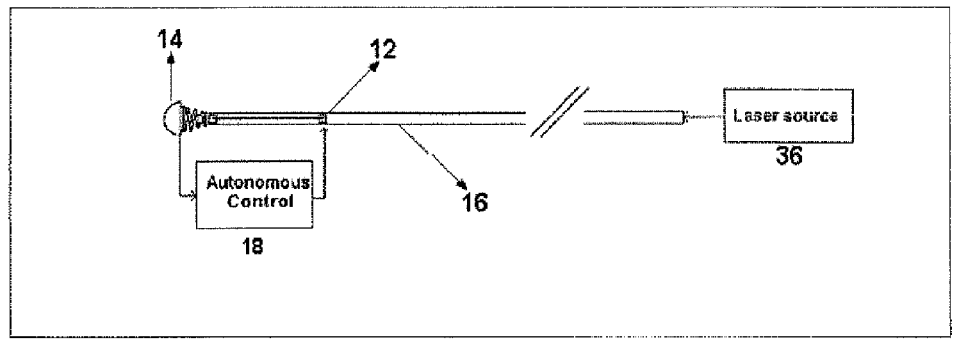
FIG. 1 is a schematic diagram of the autonomous control of the instrumented catheter constructed in accordance with the present invention.

In one embodiment, this invention describes a completely autonomous control of a catheter instrumented with Shape Memory Alloy (SMA) actuators 12 and a novel three Degree Of Freedom (DOE) force sensor 14 on the tip of the catheter 16, as shown in FIG. 1. The force sensor 14 at the tip measures the magnitude and direction of the force acting on the tip of the catheter 16 due to contact with the blood vessel when used in angioplasty. The force measured by the sensor 14 is fed to a control system to provide an input to the SMA actuators to minimize the force acting at the tip of the catheter. This way the force at the tip of the catheter is minimized to significantly reduce the likelihood of damage to epithelial cells of the blood vessel.

Figure 2:
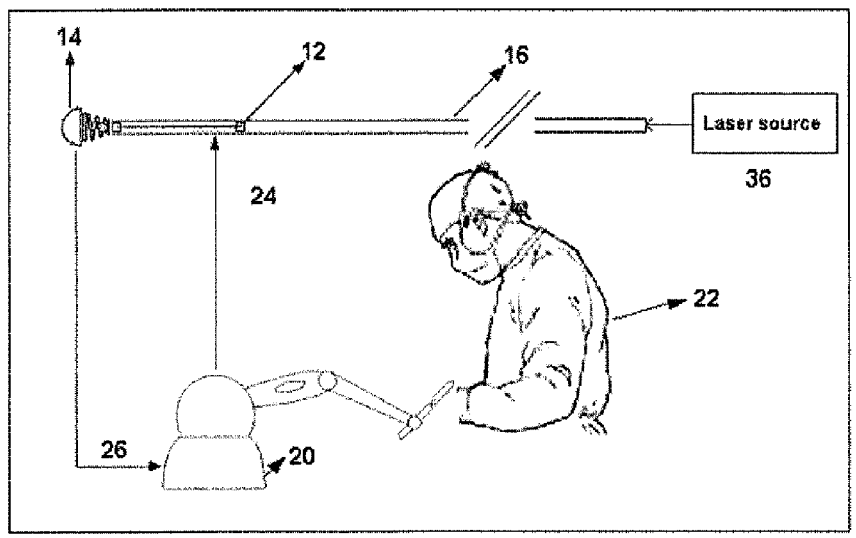
FIG. 2 is a schematic diagram of the instrumented catheter constructed in accordance with the present invention and controlled by a haptic device.

In addition, the catheter 16 instrumented with SMA actuators 12 and the 3-DOF force sensor 14 can be used as a tool to perform minimally invasive surgery and therapy at remote locations. The instrumented catheter 12 can be interfaced to a haptic device 20 in a master-slave configuration, as shown in FIG. 2. The haptic device 20 should have a minimum of 3 DOF position output 24 and force input 26. The surgeon 22, using the haptic device, provides the required position command to actuate the active catheter 16. The force felt at the tip of the catheter 16 is reflected in 3 DOFs to the haptic device 20. In this way, the surgeon 22 has access to remote sites in the blood vessel using the instrumented catheter 16. The active catheter can also be fitted with microtools at the tip to perform on-site diagnosis, biopsies or plaque removal. In addition to application in angioplasty, the catheter can also be used for fetal and gastrointestinal surgeries.

The sections below describes the design for the 3-DOF force sensor, the modeling of the Shape Memory Alloy Actuators, the LQR and $H_\infty$ loop shaping controller design, the autonomous control of the catheter, and the force reflection to a haptic device.

Sensor

Figures 3A, 3B:
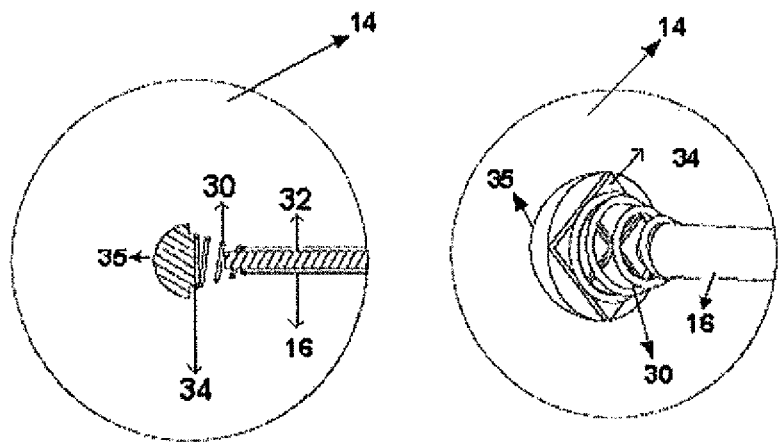
FIG. 3A is a cross sectional view of the three-dimensional force sensor of the present invention.
FIG. 3B is a perspective view of the three-dimensional force sensor of the present invention.
Figure 4:
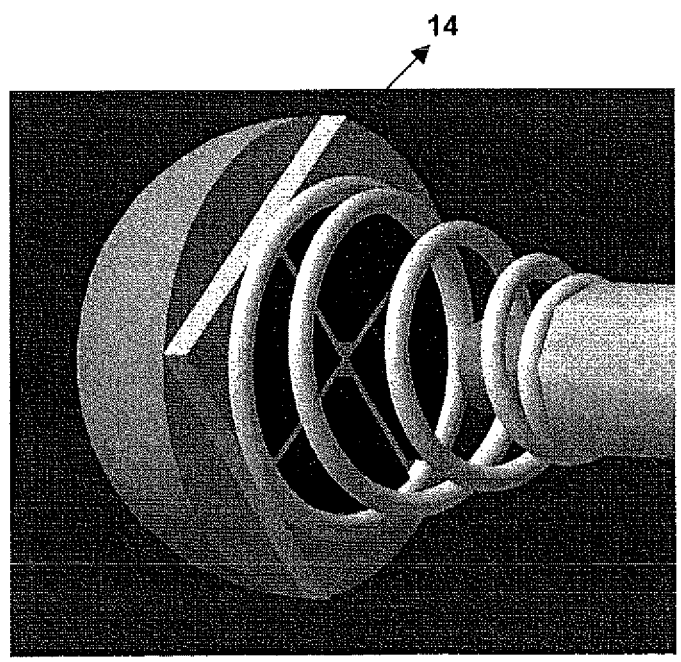
FIG. 4 is a three dimensional rendering of the three-dimensional force sensor of the present invention.

Referring to FIGS. 3 and 4, the sensor 14 designed in accordance with the present invention is a miniaturized 3-DOF force sensor which is attached to the tip of the catheter 16. The sensor 14 is capable of measuring the magnitude and direction of the force acting on the tip. The sensor 14 consists of a spring 30 preferably a conical spring (or any suitable elastic flexible material)—one end of which is attached to an optical fibre 32 which remains constrained to the catheter 16, the other end is attached to a 2-d Optical Position Sensing Detector (2d PSD) 34. The optical fibre 32 is coupled to a source of LASER 36 or a high intensity LED. The 2d PSD, which could be a quadrant detector or a lateral effect detector, consists of four independent photodetectors, which measure the intensity of light falling on it. The position sensor 34 provides four outputs from which the position of the beam spot on the surface of the PSD can be accurately calculated (FIG. 3 and FIG. 4). The position sensor 34 has a hemispherical tip 35 attached thereto.

A force acting on the sensor 14 due to contact with the walls of the blood vessel causes the spring 30 to bend. Since the optical fibre 32 and one end of the spring 30 are fixed to the catheter 16, the spring bends 30 relative to the catheter 16 and as a result the position of the beam spot from the optical fibre 32 shifts along the surface of the 2d PSD 34. The deviation of the beam spot along the surface of the 2d PSD 34 can be used to calculate the amount of bending in the spring which is proportional to the force acting on the tip of the catheter, by Hooke's Law. Therefore, the magnitude and direction of the force acting on the sensor can be measured accurately. The total voltage from all four outputs is an indication of the total intensity of light falling laterally on the PSD.

The force sensor 14 is mounted on the tip of the catheter 16. The sensor 14 measures the force exerted by the artery walls on the tip of the catheter. This force reading can be used to autonomously guide the catheter to prevent damage to the epithelial cells of the artery or it can be reflected to a haptic device.

Actuators

Figure 5:
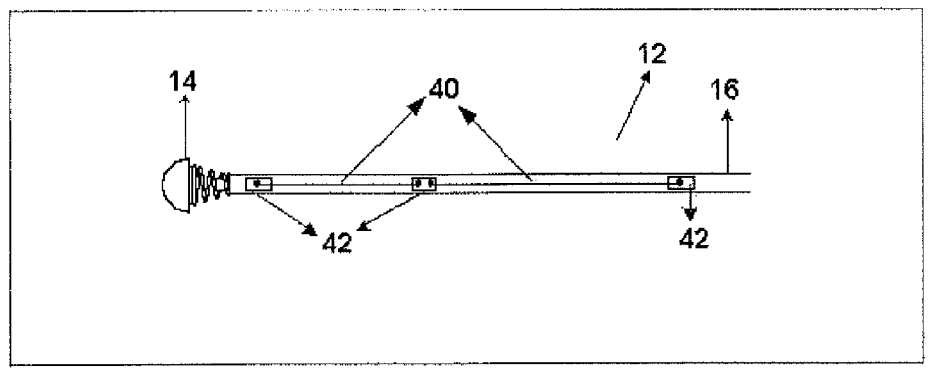
FIG. 5 is a cross sectional view of the active catheter showing multiple shape memory alloy sections.
Figure 6:
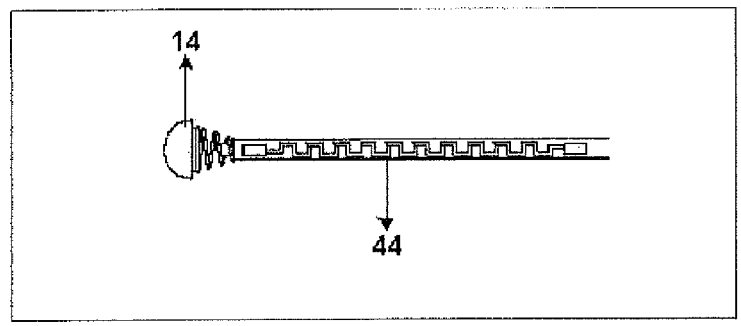
FIG. 6 is a cross sectional view of the active catheter showing patterned shape memory alloy sections.

Referring to FIGS. 5 and 6, the actuators 12 guide the catheter 14 through the lumen of the blood vessel without causing damage to the inner linings of the blood vessel. The actuators 12 also facilitate easy movement of the catheter 14 into one of the blood vessels at a branch. The actuators 12 could be made of Shape Memory Alloy (SMA) or Electro active polymers. SMA filaments (wire 40 and tube 44) are used to build the actuators 12 on the catheter 14. The property of SMAs of demonstrating a change in strain by a change in temperature is due to a solid-state phase change from the Martensite form to the Austenite form. Martensite is relatively softer and easily deformable and exists at a lower temperature. Heating by means of current or hot water results in a phase transition from the Martensite phase to the Austenite phase. In the Austenite phase, the SMA is more structured and is harder and stronger than in the Martensite phase.

The SMA actuators 12 on the instrumented catheter 16 could be either in the form of a wire, tube or sheet. Since the machinability of SMA is low, the wires or filaments 40 should be microwelded to the stainless steel pads 42 which can be glued to the catheter, as illustrated in FIG. 5. A minimum of three wires 40 placed at 120° is required to bend the catheter 16 in all directions. The bending can be created by a number of sections of SMA to create variable bending radius and angles. The example shown in FIG. 1 shows one section of the SMA with one set of three wires 40 and the example shown in FIG. 5 shows two sections each having three wires 40. SMA tubes and sheets can also be used to create the bending portion of the catheter. Patterns 44 can be laser-machined on the SMA tubes or sheets and can be directly glued to the catheter, as shown in FIG. 6.

In order to control the bending angle of the catheter, the amount of strain generated in the SMA actuators 12 should be controlled. For this, the physical behavior of the SMA should be described in dynamic equations. The model of the SMA set out below is based on the laws of physics. The modeling equations are as follows:

Modelling of Phase Transformations

Since an SMA exists in two states, it can be modelled as a two-state system. There is a similarity between this system and an electron, which can exist only in two states—the positive spin or the negative spin. The Fermi-Dirac statistics are used to describe the number of electrons in the two states depending on the energy of the electron. The state of an SMA in the Martensite and Austenite forms using the same statistics has been modeled.

Two modelling equations were used based on whether the alloy is being heated or cooled due to hysteresis with two different transition temperatures. Since the SMA is in the Martensite form at lower temperatures, the phase transformation equation during heating is described by analogy with the Fermi-Dirac statistics in the form:

$$\xi = \frac{\xi_m}{1 + \exp\left(\frac{T_{fa} - T}{\sigma_a} + K_a\sigma\right)} \quad (1)$$

where $\xi$ is the fraction of the Austenite phase, is the fraction of the Martensite phase prior to the present transformation from Martensite to Austenite, T is the temperature, $T_{fa}$ is the transition temperature from Martensite to Austenite, $v_a$ is an indication of the range of temperature around the transition temperature $T_{fa}$ during which the phase change occurs, $\sigma$ is the stress and $K_a$ is the stress curve-fitting parameter which is obtained from the loading plateau of the stress-strain characteristic with no change in temperature.

On cooling, the Austenite phase gets converted to the Martensite phase and the modelling equation during cooling is described by analogy with the Fermi-Dirac statistics in the form:

$$\xi = \frac{\xi_a}{1 + \exp\left(\frac{T_{fm} - T}{\sigma_m} + K_m\sigma\right)} \quad (2)$$

where $\xi_a$ is the fraction of the Austenite phase prior to the present transformation from Austenite to Martensite, T is the temperature, $T_{fm}$ is the transition temperature from Austenite to Martensite, $\sigma_m$ is an indication of the range of temperature around the transition temperature $T_{fm}$ during which the phase change occurs, $\sigma$ is the stress and $K_m$ is the stress curve-fitting parameter which is obtained from the unloading part of the stress-strain characteristic.

Since the SMA is modelled as a two-component system, at any given time, the sum of the mole fractions of the Austenite and Martensite phase is 1, i.e., $$\xi_a + \xi_m = 1 \quad (3)$$

The time derivatives of Eqns. (1) and (2) are as follows:

For heating:

$$\dot\xi = \frac{\xi^2}{\xi_m}\left[\exp\left(\frac{T_{fa} - T}{\sigma_a} + K_a\sigma\right)\right]\left[\frac{\dot T}{\sigma_a} - K_a\dot\sigma\right] \quad (4)$$

For cooling:

$$\dot\xi = \frac{\xi^2}{\xi_a}\left[\exp\left(\frac{T_{fm} - T}{\sigma_m} + K_m\sigma\right)\right]\left[\frac{\dot T}{\sigma_m} - K_m\dot\sigma\right] \quad (5)$$

Modelling of Temperature Dynamics

An SMA actuator is heated by the process of Joules heating by applying a voltage across the SMA. The loss of heat from the SMA is through natural convection. Mathematically the dynamics of the temperature are given by equation (6).

$$\dot T = \frac{1}{mc_p}\left[\frac{V^2}{R} - hA(T - T_a)\right] \quad (6)$$

where m is the mass per unit length, $c_p$ is the specific heat capacity, V is the voltage applied across the SMA, R is the resistance per unit length, h is the coefficient of convection, A=πd is the circumferential area of cooling, d is the diameter of the wire, T is the temperature and $T_a$ is the ambient temperature. The coefficient h is assumed to have the characteristics of a second-order polynomial to enhance the rate of convection at higher temperatures as observed in open-loop results:

$$h = h_0 + h_2 T^2 \quad (7)$$

Constitutive Equation

Figure 7:
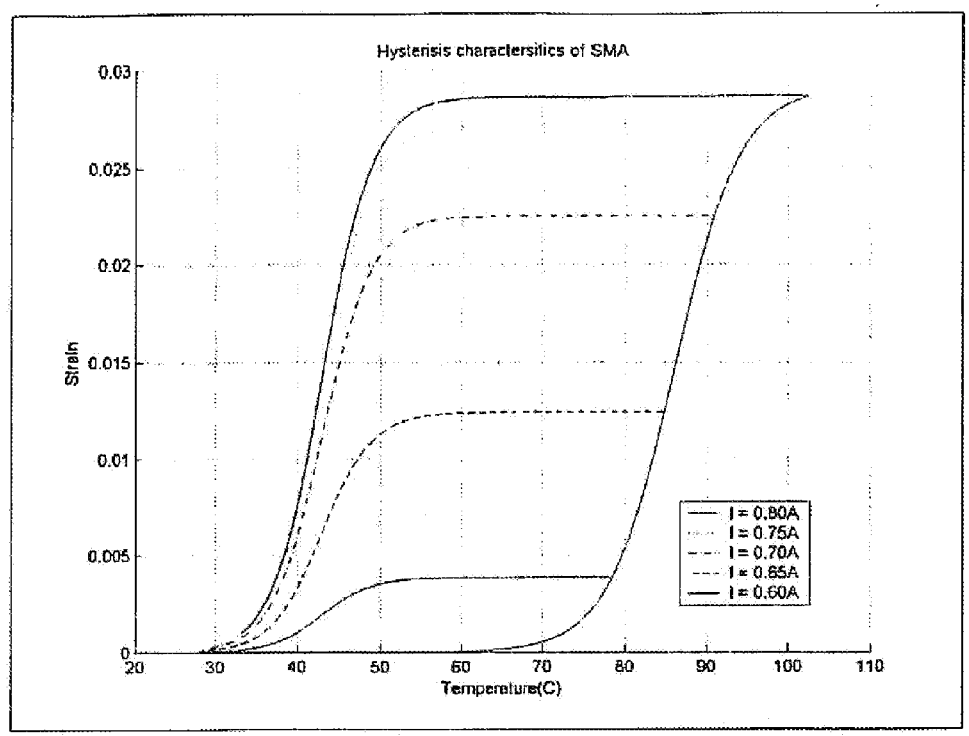
FIG. 7 is hysteresis characteristics of the shape memory alloy for varying sinusoidal input.

The constitutive equation relating changes in stress, strain, temperature and mole fraction is given by the following equation:

$$\dot\sigma = D\dot\epsilon + \theta_t\dot T + \Omega\dot\xi \quad (8)$$

where $\sigma$ is the stress in the SMA, D is the average of the Young's Moduli for the Martensite and Austenite phases, e is the strain, $\theta_t$ is the thermal expansion factor and $\Omega$ is the phase transformation contribution factor. The model explains the hysteresis as well as the minor loops in the hysteresis, as illustrated in FIG. 7.

The dynamic characteristics of the SMA are completely defined by equation (4) or (5) (heating or cooling), together with equations (6) and (8). The $\sigma_e$ is defined as the integral of the error, i.e., $$\dot\sigma_e = \epsilon - \epsilon_{ref} \quad (9)$$

where $\epsilon$ is the strain of the SMA actuator and $\epsilon_{ref}$ is the reference trajectory. The dynamic equations of the SMA along with equation (9) can be represented in the state-space form:

$$\dot{\bar z} = f(\bar z, u, t) \quad (10)$$

where $$\bar z = \begin{bmatrix} \epsilon \\ T \\ \xi \\ \sigma_e \end{bmatrix}$$

and u is the input voltage to the SMA wire. The nonlinear equations are linearized about a set of operating points ($\epsilon_0$, $T_0$, $\xi_0$, $u_0$) on the reference trajectory.

To obtain the operating points, $\epsilon_0$ is chosen as the value of the reference strain at that instant of time. $T_0$ and $\xi_0$ are obtained by integrating equations (4) or (5) and (8), depending on whether the SMA is being heated or cooled, for a given value of $\epsilon_0$. The value of $u_0$ is obtained from equation (6) for a given value of $T_0$, assuming steady-state conditions.

Equation (10) is linearized about the calculated operating points to obtain linear models in the form:

$$\dot{z} = A\bar{z} + Bu \qquad (11)$$

$$y = C\bar{z} \qquad (12)$$

where $$A = \left[\frac{\partial f}{\partial z}\right]_{\epsilon_0, T_0, \xi_0, u_0} \quad B = \left[\frac{\partial f}{\partial u}\right]_{\epsilon_0, T_0, \xi_0, u_0}$$

For the no-load case, which is the case considered here, $\sigma$ and $\dot{\sigma}$ are equal to zero. In this case, the model given by (11) is not controllable since the number of independently controllable states is only 2. On removing the uncontrollable modes, the following state space model is obtained:

$$\dot{\bar{x}} = A'\bar{x} + B'u \qquad (13)$$

where $$\bar{x} = \begin{bmatrix} \epsilon \\ \sigma_e \end{bmatrix}$$

Controller Design

The force measured by the sensor at the tip of the catheter is provided as input to the control strategy developed to provide an output to the SMA actuators to minimize the force at the tip of the catheter. The actuators could also be activated by the surgeon to guide the catheter into the branches of the blood vessel. The control scheme should provide fast and accurate control of the strain in the SMA. Two control strategies have been developed—a Gain Scheduled PI controller and a robust $H_\infty$ loop-shaping controller using normalized coprime stabilization.

Gain Scheduled Controller

For a PI controller, the feedback is of the form, $$u = -K_P(\epsilon - \epsilon_{ref}) - K_I \sigma_e + u_0 \qquad (14)$$

where $K_P$ is the proportional gain and $K_I$ is the integral gain. Writing $K = [K_P\ K_I]$, the gains are computed such that the resulting controller minimizes the quadratic cost function, $$J(u) = \int_0^\infty (x^T Q x + u^T R u) dt \qquad (15)$$

The choice of gains for minimizing J(u) are obtained by first solving for S in the algebraic Riccati equation:

$$A'^T S + SA' - SB'R^{-1}B'^T S + Q = 0 \qquad (16)$$

The matrix K is given by:

$$K = R^{-1} B'^T S \qquad (17)$$

Figure 8:
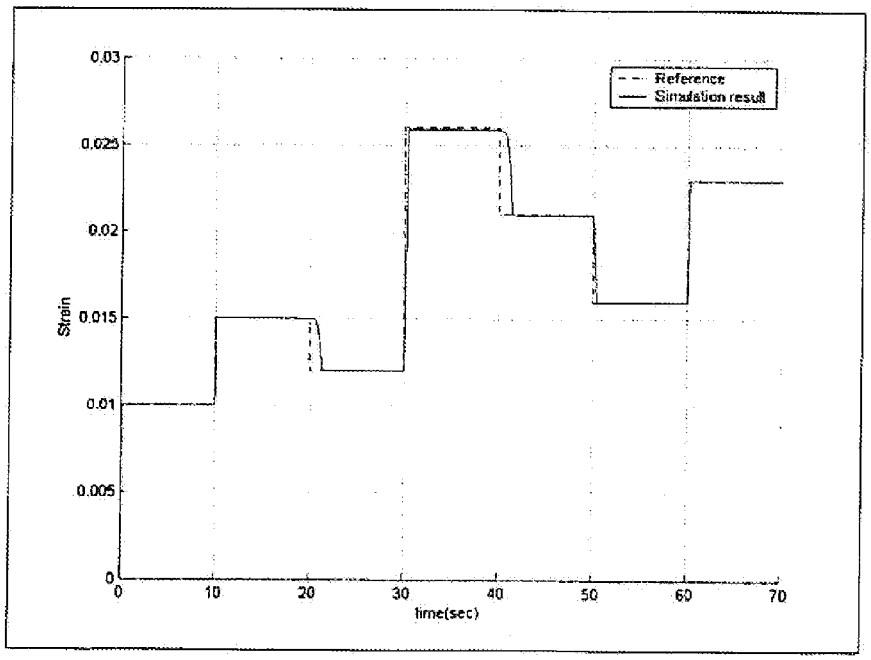
FIG. 8 is a simulated result showing a closed loop shape memory alloy response to a step reference input using the Linear Quadratic Regulator (LQR) controller.
Figure 9:
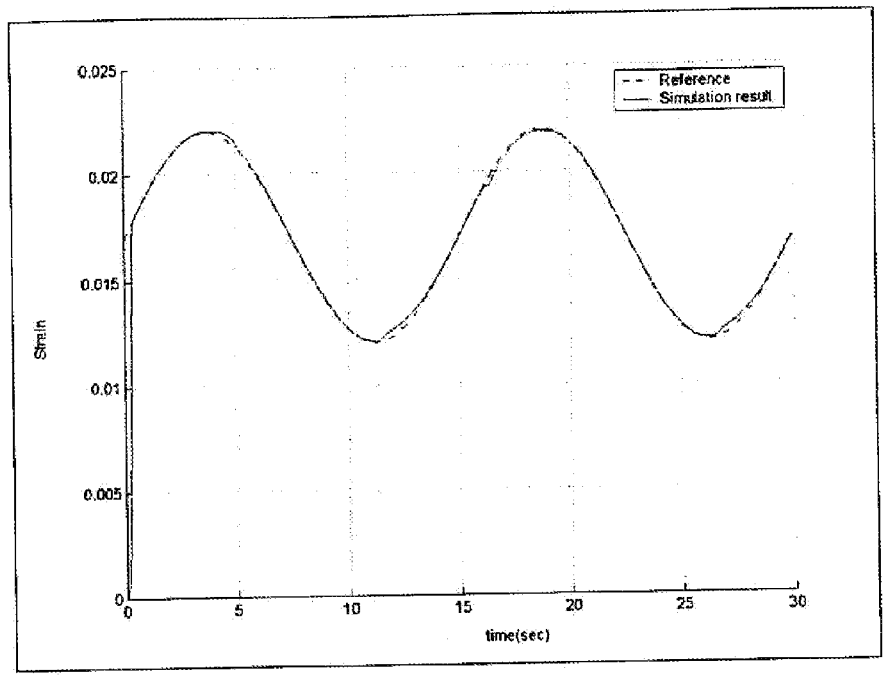
FIG. 9 is a simulated result showing a closed loop shape memory alloy response to a sinusoidal reference input using the Linear Quadratic Regulator (LQR) controller.

The simulation result for a step reference input is shown in FIG. 8 and that for a sinusoidal input is shown in FIG. 9.

Figure 10:
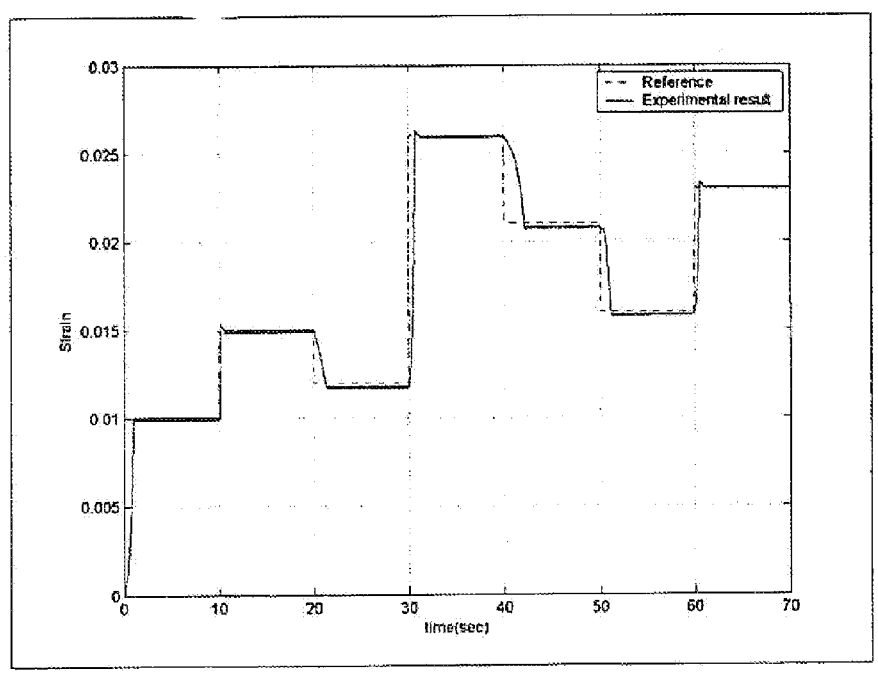
FIG. 10 is an experimental result showing a shape memory alloy response to a step reference input using the Linear Quadratic Regulator (LQR) controller.

The experimental verification of the controller was done on a 700 MHz Windows based PC at a sampling rate of about 65 Hz. Since the form of matrices A' and B' are fairly simple, the solution for the Ricatti equation was obtained in closed form using MAPLE. This also greatly reduced the computation time by avoiding matrix decompositions like the Schur decomposition. The response of the SMA to a step reference input is shown in FIG. 10.

From the experimental results, it can be observed that the response time for heating is approximately 1.0 second and for cooling is 2.1 seconds for a 0.012" diameter SMA wire. The rate of heating and cooling is much higher for a thinner wire since the ratio of surface area to volume increases as the wire diameter is reduced, thereby increasing the rate of convectional cooling.

Figure 11:
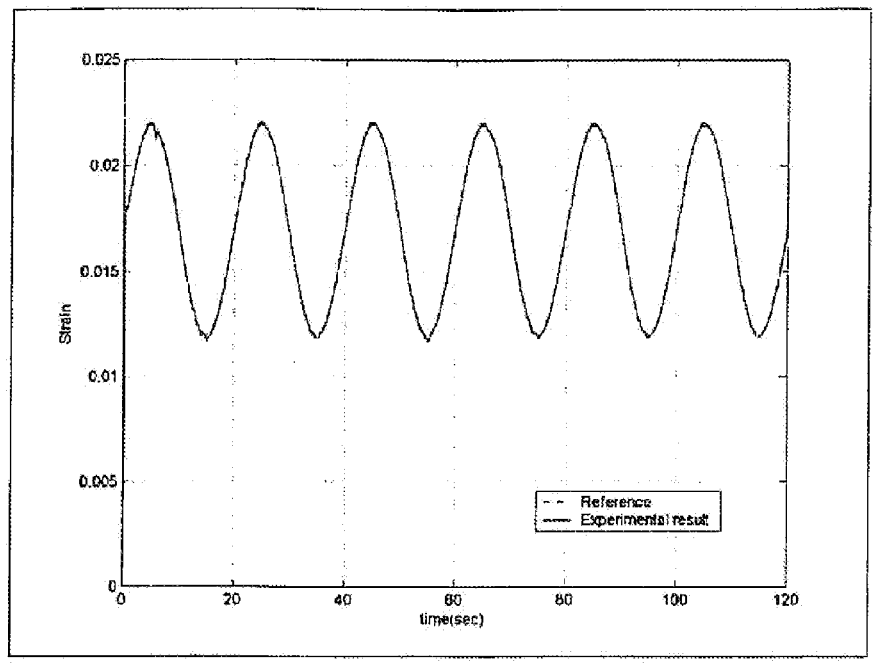
FIG. 11 is an experimental result showing a shape memory alloy response to a sinusoidal reference input using the Linear Quadratic Regulator (LQR) controller.
Figure 12:
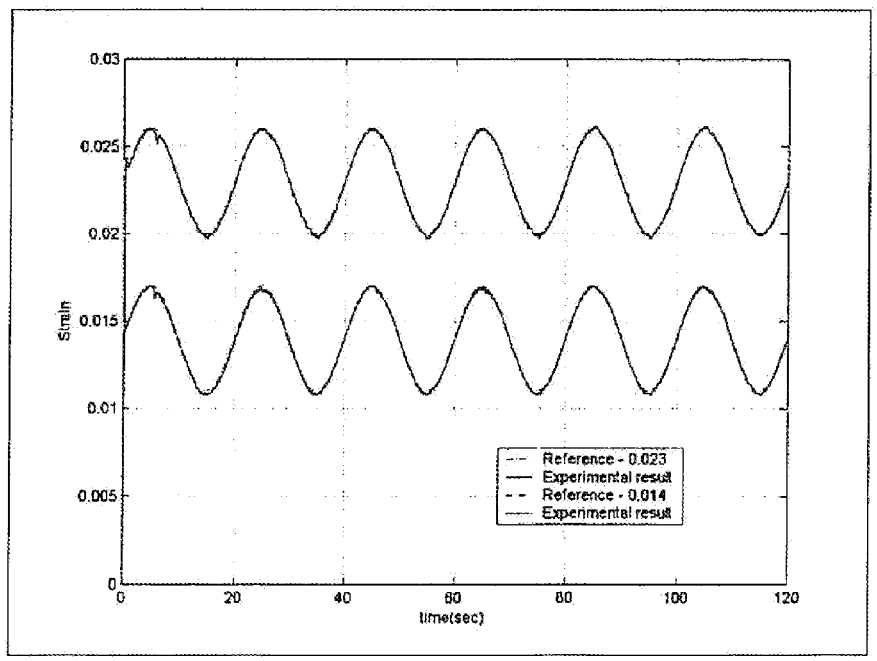
FIG. 12 is an experimental result showing a closed loop shape memory alloy responses to two sinusoidal reference inputs with different DC offsets using the Linear Quadratic Regulator (LQR) controller.
Figure 13:
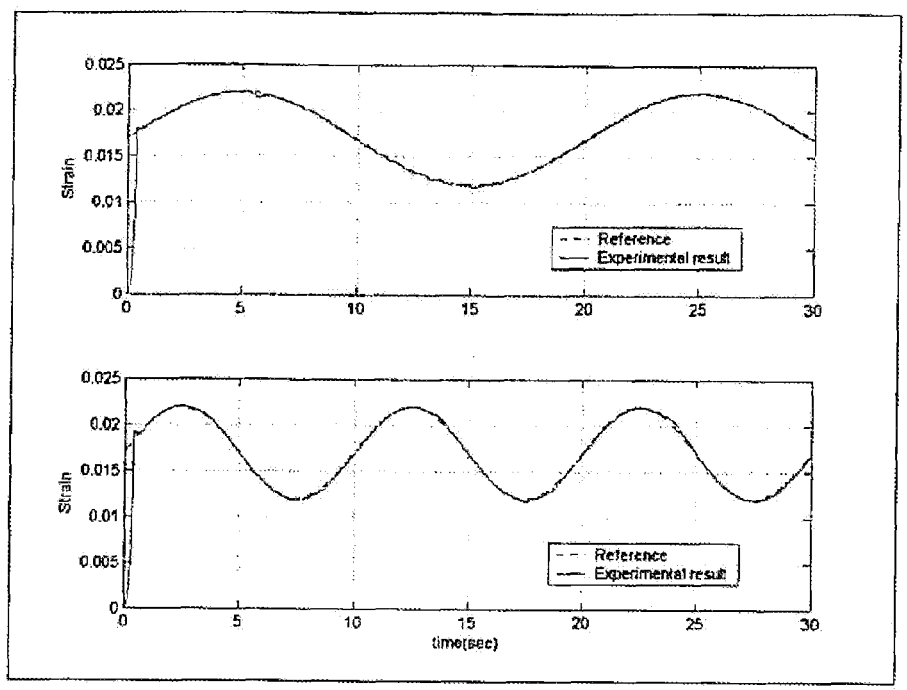
FIG. 13 is an experimental result showing a closed loop shape memory alloy responses to two sinusoidal reference inputs with different frequencies using the Linear Quadratic Regulator (LQR) controller.

The experimental result for a sinusoidal reference input is shown in FIG. 11 which shows an excellent tracking of the reference trajectory by the SMA in a closed loop. The DC offset of the reference was also varied to check the performance of the controller in the entire operating range. The results are shown in FIG. 12. The graphs show an excellent response over the entire operating region. The frequency for the reference input was also varied to check the performance of the controller and the SMA. The results are shown in FIG. 13. The response of the controller is satisfactory for frequencies lower than 0.1 Hz.

Robust Controller

The LQR based PI controller shows excellent response to a step and a sinusoidal reference input. The controller also has a good stability margin, thereby making the control law fairly insensitive to uncertainties in the parameters of the model. However, the controller is sensitive to unmodelled dynamics at high frequencies and thereby could lead to instability. For this reason, an $H_\infty$ loop-shaping controller using normalized coprime stabilization is designed such that the gains are high when the model describes the SMA accurately and low at higher frequencies when the model is inaccurate. The loop-shaping controller, however, obtains a performance/robust stability tradeoff.

The gain matrix $K = [K_P\ K_I]$ of the PI controller, as given by equation (14), is computed by the loop-shaping procedure using normalized coprime stabilization.

The nominal plant (SMA) is first shaped by using a pre-compensator $W_1$ so that the singular values of the nominal plant G are shaped to a desired open-loop shape. The compensator also ensures that the shaped plant $G_s = GW_1$ is square and $G_s$ has no hidden modes.

For ensuring robust stabilization, $\epsilon_{max}$ is calculated as, $$\epsilon_{max} = \left(\inf_{K stabilizing}\left\|\begin{bmatrix} I \\ K \end{bmatrix}(I + G_s K)^{-1} \tilde{M}_s^{-1}\right\|_\infty\right)^{-1} \qquad (18)$$

$$= \sqrt{1 - \|[\tilde{N}_s\ \tilde{M}_s]\|_H^2} < 1 \qquad (19)$$

where $\tilde{M}_s$ and $\tilde{N}_s$ define the normalized coprime factors of $G_s$. An $\epsilon = \epsilon_{max}$ is selected to form a stabilizing controller $K_\infty$, which satisfies:

$$\left\|\begin{bmatrix} I \\ K_\infty \end{bmatrix}(I + G_s K_\infty)^{-1} \hat{M}_s^{-1}\right\|_\infty \leq \epsilon^{-1} \doteq \gamma \qquad (20)$$

The final feedback controller K is obtained as the product of the precompensator $W_1$ and the $H_\infty$ controller $K_\infty$ i.e.

$$K = W_1 K_\infty \qquad (21)$$

The simulation of the robust controller and the SMA was done on MATLAB™. The desired loop shape was chosen so that the gains are high at low frequencies where the model describes the SMA accurately and the gains roll off at −20 dB beyond the corner frequency, thereby ensuring a low gain at high frequencies.

Figure 14:
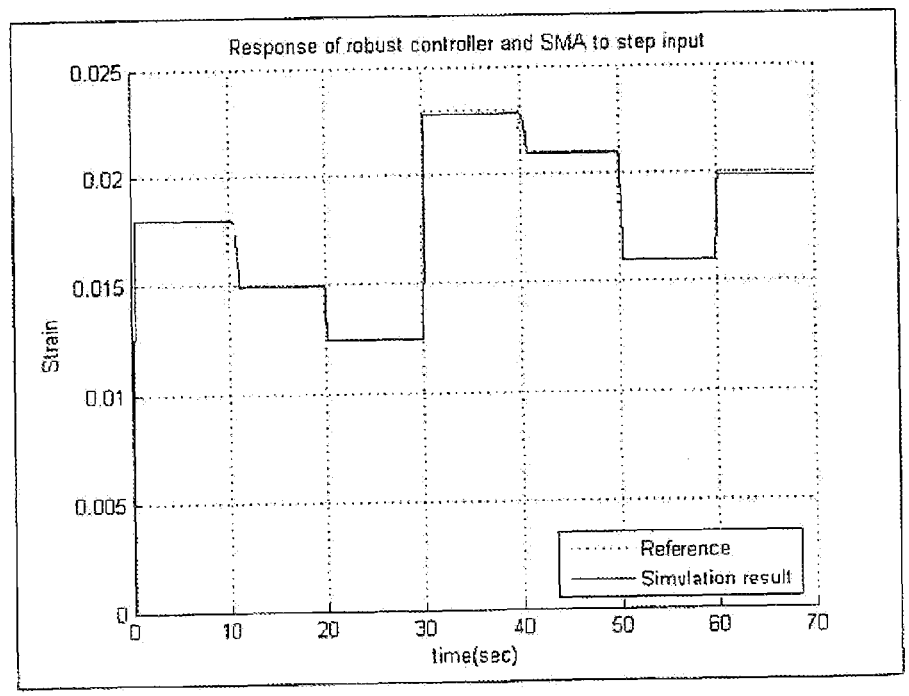
FIG. 14 is a simulation result showing a closed loop shape memory alloy responses to a step reference input using the $H_\infty$ loop-shaping controller
Figure 15:
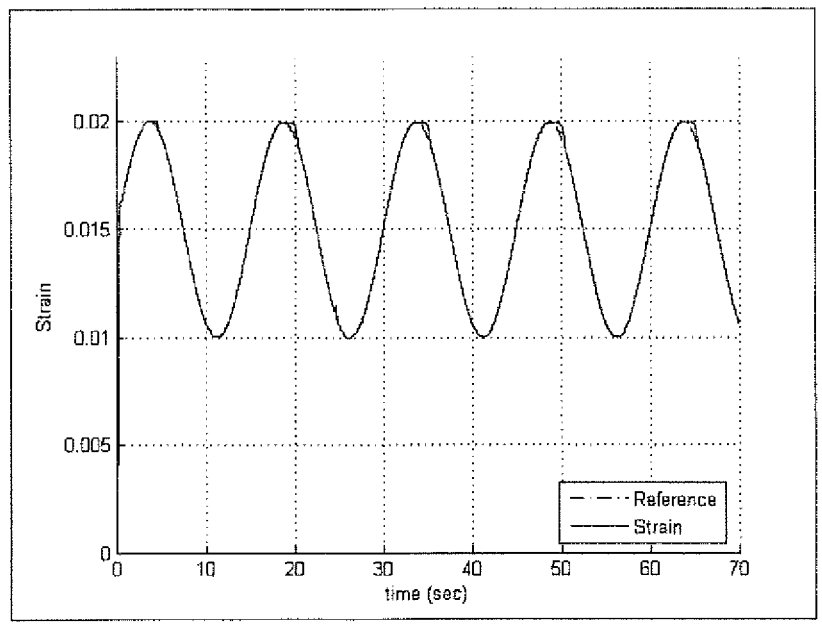
FIG. 15 is a simulation result showing a closed loop shape memory alloy response to a sinusoidal reference input using the $H_\infty$ loop-shaping controller.

The value of the corner frequency was chosen to be 1000.424 rad·sec$^{-1}$. The simulation result for input consisting of step changes is shown in FIG. 14 and for a sinusoidal reference input is shown in FIG. 15.

Figure 16:
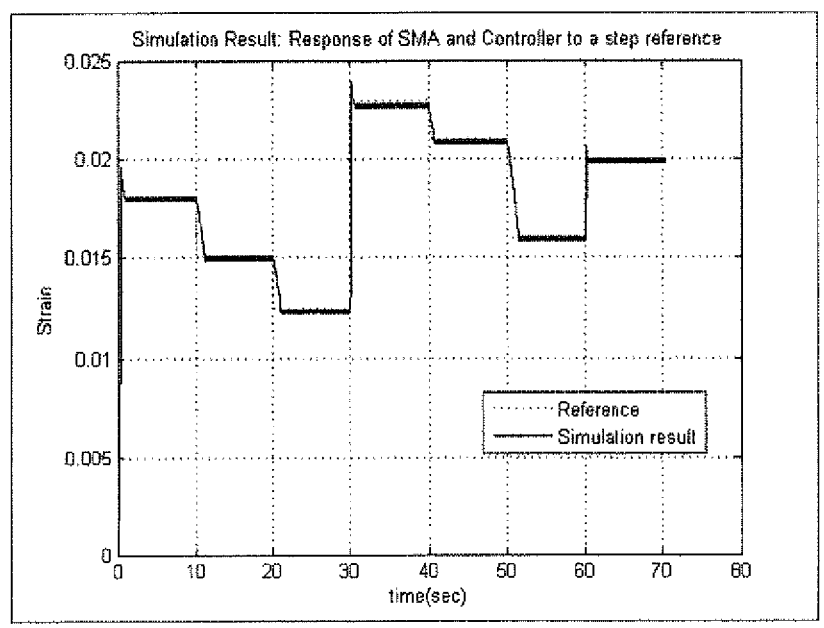
FIG. 16 is an experimental result showing a shape memory alloy response to a step reference input using the $H_\infty$ loop-shaping controller.
Figure 17:
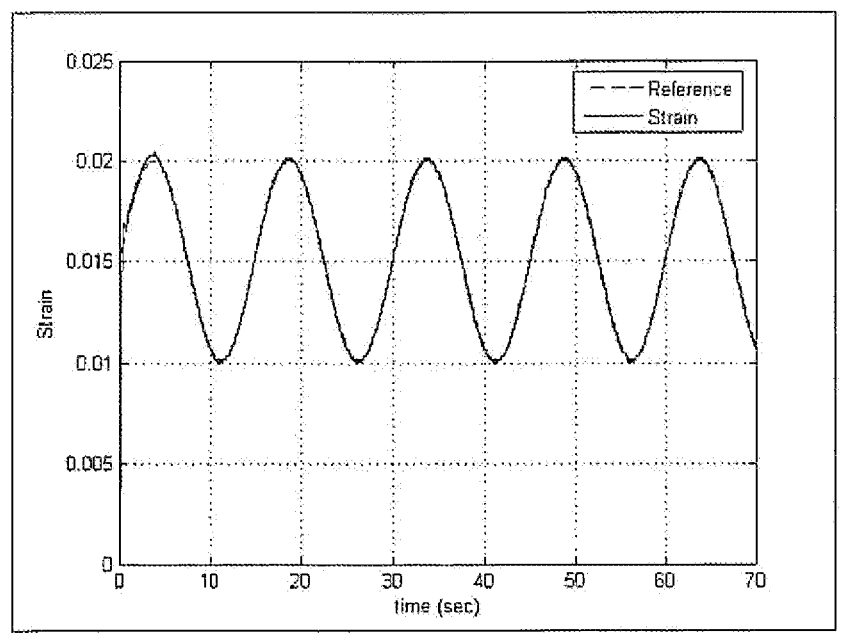
FIG. 17 is an experimental result showing a shape memory alloy response to a sinusoidal reference input using the $H_\infty$ loop-shaping controller.

The experimental verification of the controller was done on a 700 MHz Windows based PC at a sampling rate of about 100 Hz. The response of the SMA to step changes is shown in FIG. 16 and for sinusoidal reference input is shown in FIG. 17.

Autonomous Control of the Active Catheter

In the previous section, modeling and robust control of SMA actuators have been described. The simulation and experimental results show excellent tracking response for the SMA, thereby validating both the model and the control scheme. In autonomous control of an active catheter 16 fitted with SMA actuators 12 and a 3-DOF force sensor 14, the force acting on the tip of the catheter 16 is regulated so that there is no damage to the epithelial cells of the artery. A force control algorithm is implemented to ensure that the tip interaction forces are minimized.

Figure 18:
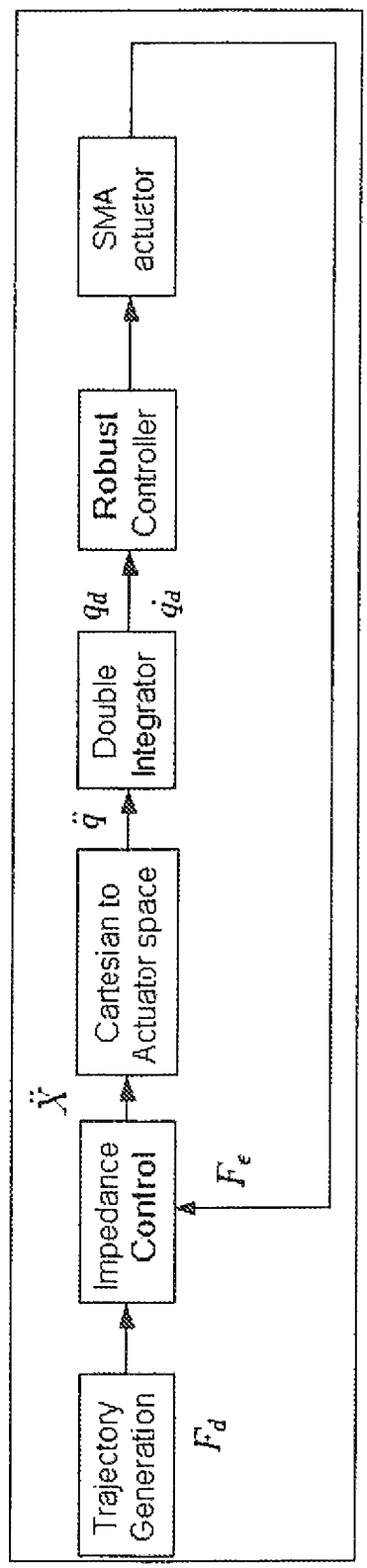
FIG. 18 is a block diagram of a force control for autonomous guidance for the catheter of the present invention.
Figure 19:
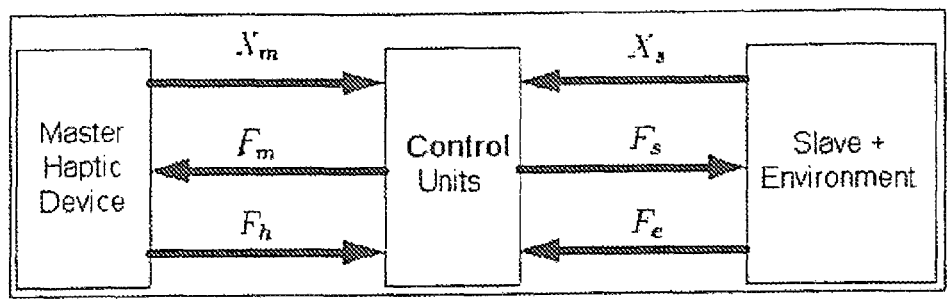
FIG. 19 is a block diagram of a master-slave configuration for the catheter of the present invention.

The miniature force sensor 14 at the tip of the catheter provides the magnitude and direction of the force acting on the tip. This force is provided as a negative feedback signal to the robust control system, as shown in FIG. 18. The sampling rate of the control algorithm is 100 Hz, providing fast response to minimize the error between the force signal $F_e$ and the desired force $F_d$. The autonomous control of an SMA actuator 12 based on the force felt at the tip prevents any damage to the epithelial cells of the arteries. In addition, the catheter autonomously guides itself in the proximity of the blockage to prevent accidental dislodging of the plaque due to application of excessive force. This ensures a higher success rate of performing angioplasty by reducing the risk of rupturing blood vessels or dislodging plaque, which can cause a stroke or myocardial infarction if the plaque lodges itself in minute arteries of the heart or the brain.

Force Reflection to a Haptic Device

One of the major problems with the conventional way of performing angioplasty is restenosis. In nearly 40% of procedures, the plaque begins to rebuild at the site after a couple of years, causing an obstruction to blood flow. In addition, the superelastic stent used for reopening the blood vessel has a lifetime of only 10 years. Therefore, the patient would have to undergo multiple angioplasties during his/her life time. A solution to this problem is to perform microsurgery at the site of the blockage.

Figure 20:
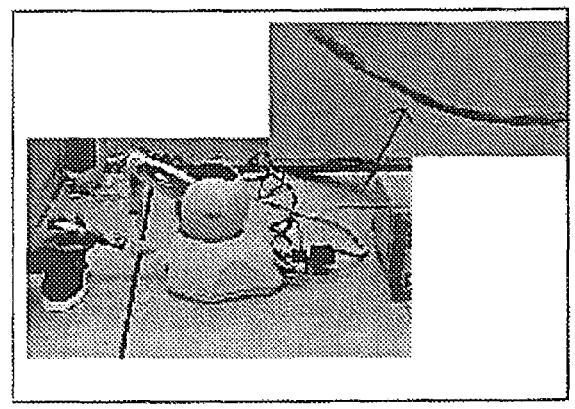
FIG. 20 is a picture of the haptic device for controlling the catheter of the present invention.
Figure 21:
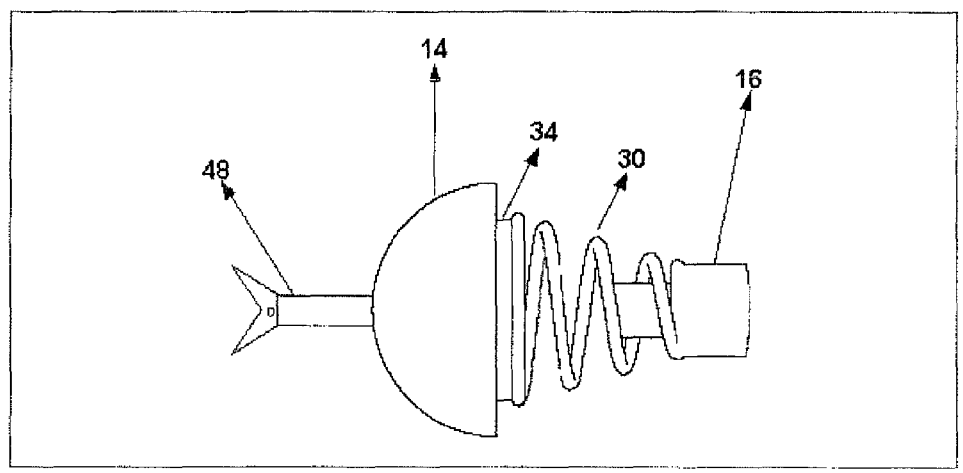
FIG. 21 is a cross-sectional diagram of the three-dimensional force sensor of the present invention and showing a surgical tool attached thereto.

The active catheter 16 fitted with SMA actuators 12 and a 3-DOF force sensor 14 can be controlled by a master haptic device 20, as shown in FIG. 2 and FIG. 20. The haptic device 20 provides position commands to the SMA actuators 12. A minimum of 3 DOFs in position and force are required for the haptic device 20. An inverse dynamics control scheme under image guidance is used to control the bending of the active catheter. The force acting on the tip of the catheter 16 is reflected to the stylus of the haptic device 20. The surgeon can, therefore, feel these forces caused by interactions between the catheter 16 and the artery walls. In none of the technologies developed thus far has the surgeon had the capability of feeling the forces exerted on the tip of the catheter at a remote location. Micro tools 48 can be attached to the tip of the catheter 16 with 3 DOF position control and the ability to feel forces, also in 3 DOF. Using these tools, the surgeon can gently remove the plaque from the site under image guidance and force feedback, thereby leading to a permanent treatment of plaque buildup. This tool can also be used to perform various procedures like biopsies and on-site diagnosis, as shown in FIG. 21.

In addition to the application in Angioplasty, the instrumented catheter 16 can also be used to perform minimally invasive fetal surgery. An abnormality can arise in some fetuses where the diaphragm separating the chest cavity from the abdomen does not completely develop. As a result the intestines begin to grow in the chest cavity, preventing the development of the lungs. This abnormality is called Congenital Diaphragmatic Hernia (CDH). In such cases, the surgeon can perform "fetal endoscopic surgery" for CDH. In this procedure, a catheter along with surgical instruments is inserted through tiny ports in the mother's womb. The surgeon operates on the fetus entirely within the womb. The trachea of the fetus is clipped to block the windpipe. This causes the trapped liquid in the lungs to aid in the growth and expansion of the lungs. This is a high risk operation and requires high dexterity and maneuverability on the part of the surgeon to position the fetus and the mother accurately. In addition, it is extremely difficult to operate on a fetus floating in the amniotic fluid without any force or visual feedback. However, the procedure is safer for the mother and the fetus in comparison to open fetal surgery, where a large incision must be made in the uterus and in the amniotic sac, since it reduces the chances of pre-term labor. A premature birth would reduce the amount of time for the fetus to develop in the womb after prenatal surgery, and reduce its chances of survival.

An instrumented catheter 16 as described in the invention would be useful in guiding the catheter into the windpipe of the fetus under image and haptic guidance. This would reduce the time taken and the chances of injury to the fetus in inserting the instrumented catheter 16 into the fetus, thereby making the procedure more reliable and efficient and reducing the amount of stress to the surgeon.

The primary application of this invention is to insert a catheter instrumented 16 with a 3-DOF force sensor 14 and Shape Memory Alloy actuators 12 smoothly into an artery and guide it through the lumen of the blood vessel till the catheter 16 reaches a blockage. The stent is then deployed to resume normal blood flow. The 3-Degrees of Freedom (DOF) force sensor 14 measures the magnitude and direction of the force being applied. It could be used for a number of other applications. Specifically it could be used at the tip of a catheter to measure the forces exerted by the walls of the blood vessel on the tip of the catheter. It could also be used as a minimally invasive tool to measure the force exerted by the tool during surgery. As well it could be used to study soft tissue properties by measuring accurately the forces exerted by the soft tissue during deformation of the tissue.

The Shape Memory alloy actuators 12 have a number of advantages. Specifically, SMA actuators have large plastic deformations which can be recovered; can generate large load forces; have high power to weight ratio; have low driving voltages; have no moving parts; are noiseless; can be used in compact workspace; and are biocompatible and corrosion resistant.

The modeling and accurate control of the SMA actuators 12 enables its use for a number of applications. Specifically it could be used as an active catheter, biomedical forceps, tissue stapler, stent, and minimally invasive, tools.

As used herein, the terms "comprises" and "comprising" are to be construed as being inclusive and opened rather than exclusive. Specifically, when used in this specification

What is claimed as the invention is:

1. A system for controlling a thin flexible thermoplastic catheter comprising:
   a plurality of shape memory alloy filaments attached to the distal end of the catheter, each filament having a solid-state phase and a temperature, wherein the catheter is of a size configured for insertion into the blood vessel;
   a means for receiving a strain value for at least one of the filaments;
   a means for determining a solid-state phase change that will result in the strain value, whereby the solid-state phase change is dependent on the temperature and the temperature is dependent on a voltage; and
   a means for setting the voltage in each filament thereby resulting in bending of the catheter in three dimensional space,
   wherein the temperature is determined using a formula given by $$\dot{T} = \frac{1}{mc_p}\left[\frac{V^2}{R} - hA(T - T_a)\right]$$

where m is the mass per unit length, $c_p$ is the specific heat capacity, V is the voltage applied across the shape memory alloy filament, R is the resistance per unit length, h is the coefficient of convection, $A=\pi d$ is the circumferential area of cooling, d is the diameter of the filament, T is the temperature and $T_a$ is the ambient temperature.

2. A system as claimed in claim 1 wherein the strain value is determined by a user.

3. A system as claimed in claim 1 wherein the plurality of filaments include three filaments equally spaced around the catheter.

4. A system as claimed in claim 3 wherein each filament is micro-machined into a predetermined pattern and each filament is attached to the catheter along its length.

5. A system as claimed in claim 3 wherein each filament is an elongate filament attached to the catheter at each end thereof.

6. A system as claimed in claim 5 wherein the plurality of filaments is a first set of filaments and further including a second set of filaments wherein the second set of filaments are adjacent to the first set of filaments along the catheter.

7. A system as claimed in claim 5 wherein the plurality of filaments is a first set of filaments and further including a second set of filaments wherein the second set of filaments is spaced a predetermined space from the first set of filaments along the catheter.

8. A system as claimed in claim 1 wherein the catheter is used in one of heart surgery, gastrointestinal surgery and fetal surgery.

9. A system as claimed in claim 1 where the strain is determined using a formula given by $$\dot{\sigma} = D\dot{\epsilon} + \theta_t \dot{T} + \Omega \dot{\xi}$$

where σ is the stress in the filament, D is the average of the Young's Moduli for the Martensite and Austenite phases, ε is the strain, $\theta_t$ is the thermal expansion factor, and Ω is the phase transformation contribution factor.

10. A system as claimed in claim 9 wherein the mole fraction of shape memory alloy filament in the Austenite phase while heating is determined using a formula given by:

$$\dot{\xi} = \frac{\xi^2}{\xi_m}\left[\exp\left(\frac{T_{fa} - T}{\sigma_a} + K_a\sigma\right)\right]\left[\frac{\dot{T}}{\sigma_a} - K_a\dot{\sigma}\right]$$

where ξ is the fraction of the Austenite phase, $\xi_m$ is the fraction of the Martensite phase prior to the present transformation from Martensite to Austenite, T is the temperature, $T_{fa}$ is the transition temperature from Martensite to Austenite, $\sigma_a$ is an indication of the range of temperature around the transition temperature $T_{fa}$ during which the solid-state phase change occurs, σ is the stress and $K_a$ is the stress curve-fitting parameter which is obtained from the loading plateau of the stress-strain characteristic with no change in temperature; and
the mole fraction of shape memory alloy filament in the Austenite phase while cooling is determined using the formula given by:

$$\dot{\xi} = \frac{\xi^2}{\xi_a}\left[\exp\left(\frac{T_{fm} - T}{\sigma_m} + K_m\sigma\right)\right]\left[\frac{\dot{T}}{\sigma_m} - K_m\dot{\sigma}\right]$$

where $\xi_a$ is the fraction of the Austenite phase prior to the present transformation from Austenite to Martensite, T is the temperature, $T_{fm}$ is the transition temperature from Austenite to Martensite, $\sigma_m$ is an indication of the range of temperature around the transition temperature $T_{fm}$ during which the solid-state phase change occurs, σ is the stress and $K_m$ is the stress curve-fitting parameter which is obtained from the unloading part of the stress-strain characteristic.

11. A system as claimed in claim 10 wherein the strain in the filament is controlled by means of a gain scheduled Linear Quadratic Regulator control, which is done by optimizing the cost function, $$J(u) = \int_0^\infty (x^T Q x + u^T R u) dt$$

where $$\bar{x} = \begin{bmatrix} \epsilon \\ \sigma_e \end{bmatrix}$$

ε is the strain and $\sigma_e$ is the integral of error, u is the voltage input, Q and R are positive definite matrices.

12. A system as claimed in claim 10 wherein the strain in the filament is controlled by means of a robust $H_\infty$ loop shaping controller to ensure robust stability and performance.

13. A system as claimed in claim 1 further including a force sensor attached to the distal end of the catheter and a means for receiving a signal from the force sensor.

14. A system as claimed in claim 13 wherein the force sensor measures forces in three degrees of freedom.

15. A system as claimed in claim 14 wherein the sensor includes:
a two-dimensional optical position sensing detector located at a predetermined distance from the distal end of the catheter;
a spring attaching the detector to the catheter whereby force on the detector moves the detector relative to the distal end of the catheter;
a light source located at the end of the catheter is coupled to an optical fibre whereby the light source emits a beam spot; and
a means for determining the position of the beam spot on the detector.

16. A system as claimed in claim 14 wherein the signal from the force sensor is used to determine the strain value such that the distal end of the catheter is deflected autonomously to minimize the force on the tip of the catheter when the signal from the force sensor is over a predetermined value.

17. A system as claimed in claim 14 further including a haptic device operably connected to the plurality of filaments and the force sensor; wherein the haptic device transmits strain values to the plurality of filaments and receives the signal from the force sensor.

18. A system as claimed in claim 15 further including a hemispherical tip attached to the detector extending outwardly from the detector away from the spring.

19. A system as claimed in claim 18 further including a means for determining the intensity of the light on the detector.

20. A system as claimed in claim 15 wherein the two-dimensional optical position detector is a quadrant detector.

21. A system as claimed in claim 15 wherein the two-dimensional optical position detector is a lateral-effect detector.

22. A system as claimed in claim 18 wherein the spring is a conical spring.

23. A system as claimed in claim 15 wherein the light source is a laser.

24. A system as claimed in claim 15 wherein the light source is a high intensity light emitting diode.

25. A system as claimed in claim 13 wherein the sensor further includes a surgical tool extending outwardly therefrom.

26. A method of controlling a catheter having a plurality of shape memory alloy filaments comprising the steps of:
receiving a strain value for at least one of the filaments attached at the distal end of the catheter, wherein the catheter is of a size configured for insertion into the blood vessel;
determining a solid state phase change that will result in the strain value, whereby the solid state phase change is dependent on the temperature and the temperature is dependent on a voltage; and
setting the voltage in each filament thereby resulting in bending of the catheter in three dimensional space,
wherein the temperature is determined using a formula given by $$\dot{T} = \frac{1}{mc_p}\left[\frac{V^2}{R} - hA(T - T_a)\right]$$

where m is the mass per unit length, $c_p$ is the specific heat capacity, V is the voltage applied across the shape memory alloy filament, R is the resistance per unit length, h is the coefficient of convection, $A = \pi d$ is the circumferential area of cooling, d is the diameter of the filament, T is the temperature and $T_a$ is the ambient temperature.

27. A method of controlling a catheter as claimed in claim 26 wherein the mole fraction of shape memory alloy filament in the Austenite phase while heating is determined using a formula given by:

$$\dot{\xi} = \frac{\xi^2}{\xi_m}\left[\exp\left(\frac{T_{fa} - T}{\sigma_a} + K_a\sigma\right)\right]\left[\frac{\dot{T}}{\sigma_a} - K_a\dot{\sigma}\right]$$

where $\xi$ is the fraction of the Austenite phase, $\xi_m$ is the fraction of the Martensite phase prior to the present transformation from Martensite to Austenite, T is the temperature, $T_{fa}$ is the transition temperature from Martensite to Austenite, $\sigma_a$ is an indication of the range of temperature around the transition temperature $T_{fa}$ during which the solid-state phase change occurs, $\sigma$ is the stress and $K_a$ is the stress curve-fitting parameter which is obtained from the loading plateau of the stress-strain characteristic with no change in temperature; and
the mole fraction of shape memory alloy filament in the Austenite phase while cooling is determined using the formula given by:

$$\dot{\xi} = \frac{\xi^2}{\xi_a}\left[\exp\left(\frac{T_{fm} - T}{\sigma_m} + K_m\sigma\right)\right]\left[\frac{\dot{T}}{\sigma_m} - K_m\dot{\sigma}\right]$$

where $\xi_a$ is the fraction of the Austenite phase prior to the present transformation from Austenite to Martensite, T is the temperature, $T_{fm}$ is the transition temperature from Austenite to Martensite, $\sigma_m$ is an indication of the range of temperature around the transition temperature $T_{fm}$ during which the solid-state phase change occurs, $\sigma$ is the stress and $K_m$ is the stress curve-fitting parameter which is obtained from the unloading part of the stress-strain characteristic.

28. A method of controlling a catheter as claimed in claim 27 where the strain is determined using a formula given by $$\dot{\sigma} = D\dot{\epsilon} + \theta_t\dot{T} + \Omega\dot{\xi}$$

where $\sigma$ is the stress in the filament, D is the average of the Young's Moduli for the Martensite and Austenite phases, $\epsilon$ is the strain, $\theta_t$ is the thermal expansion factor, and $\Omega$ is the phase transformation contribution factor.

29. A method of controlling a catheter as claimed in claim 28 wherein the strain in the filament is controlled by means of a gain scheduled Linear Quadratic Regulator control, which is done by optimizing the cost function, $$J(u) = \int_0^\infty (x^T Q x + u^T R u) dt$$

where $$\bar{x} = \begin{bmatrix} \epsilon \\ \sigma_e \end{bmatrix}$$

$\epsilon$ is the strain and $\sigma_e$ is the integral of error, u is the voltage input, Q and R are positive definite matrices.

30. A method of controlling a catheter as claimed in claim 29 wherein the strain in the filament is controlled by means of a robust $H_\infty$ loop shaping controller to ensure robust stability and performance.

31. A method of controlling a catheter as claimed in claim 26 wherein the catheter has a force sensor at the distal end thereof and further including the step of receiving a signal from the force sensor.

32. A method of controlling a catheter as claimed in claim 31 further including the step of determining the strain value from the signal received from the force sensor.

33. A method of controlling a catheter as claimed in claim 31 wherein the strain value is received from a haptic device and further including the step of transmitting the signal from the force sensor to the haptic device.

* * * * *